"(12) United States Patent
Gazmuri

(10) Patent No.: US 8,067,366 B2
(45) Date of Patent: *Nov. 29, 2011

(54) FACILITATION OF RESUSCITATION FROM CARDIAC ARREST BY ERYTHROPOIETIN

(75) Inventor: Raul J. Gazmuri, Chicago, IL (US)

(73) Assignee: Rosalind Frankling University of Medicine and Science, North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/613,919

(22) Filed: Nov. 6, 2009

(65) Prior Publication Data

US 2010/0130407 A1    May 27, 2010

Related U.S. Application Data

(63) Continuation-in-part of application No. 11/489,846, filed on Jul. 20, 2006.

(60) Provisional application No. 61/198,731, filed on Nov. 7, 2008.

(51) Int. Cl.
*A61K 38/18*    (2006.01)
*C07K 14/505*    (2006.01)

(52) U.S. Cl. .................. 514/7.7; 530/395; 514/16.4

(58) Field of Classification Search .......... None
See application file for complete search history.

(56) References Cited

U.S. PATENT DOCUMENTS 3,552,390 A * 1/1971 Muller .......................... 601/97
7,309,687 B1 * 12/2007 Brines et al. .................. 514/2
2003/0104988 A1 * 6/2003 Brines et al. .................. 514/8

OTHER PUBLICATIONS

Mitra et al. N-linked oligosaccharides as outfitters for glycoprotein folding, form and function. TRENDS in Biochemical Sciences, vol. 13 No. 3:156-163 (2006).*
Boissel et al. Erythropoietin structure-function relationships. The Journal of Biological Chemistry, vol. 268, No. 21:15983-15993 (1993).*

* cited by examiner

*Primary Examiner* — Elizabeth C Kemmerer
*Assistant Examiner* — Regina M Deberry
(74) *Attorney, Agent, or Firm* — Joseph A. Fuchs; Avani C. Macaluso; Rockey, Depke & Lyons, LLC

(57) ABSTRACT

The present invention relates generally to the use of erythropoietin (EPO) to facilitate resuscitation from cardiac arrest. For a mammalian subject suffering from cardiac arrest, concurrent administration of EPO with resuscitation after the onset of ventricular fibrillation facilitates the resuscitation. Administration of EPO serves to attenuate myocardial abnormalities caused by cardiac arrest and the resuscitation efforts and favor improved resuscitation outcomes. The main effect of EPO that facilitates resuscitation is the preservation of left ventricular myocardial distensibility leading to improve left ventricular preload and the amount of blood ejected by chest compression. This effect enables higher coronary perfusion pressures to be generated resulting in a higher rate of return of spontaneous circulation and higher survival rates. The very same effect enables the return of spontaneous circulation to occur faster reducing the time a human subject is in cardiac arrest. These effects lead to a higher number of cardiac arrest victims to survive and to do so with intact neurological function in most of the survivors.

15 Claims, 4 Drawing Sheets"

FACILITATION OF RESUSCITATION FROM CARDIAC ARREST BY ERYTHROPOIETIN

CROSS-REFERENCE TO RELATED APPLICATIONS

This application claims priority to U.S. Provisional Patent Application Ser. No. 61/198,731 filed on Nov. 7, 2008 and is also a continuation-in-part application of U.S. patent application Ser. No. 11/489,846 filed on Jul. 20, 2006 which claims priority to U.S. Provisional Patent Application Ser. No. 60/701,731 filed on Jul. 22, 2005, the entire disclosures of which are incorporated herein by reference. Priority to this application is claimed under 35 U.S.C. §§119 and/or 120.

FIELD OF THE INVENTION

The present invention relates generally to the use of erythropoietin (EPO) to facilitate resuscitation from cardiac arrest and improve survival with neurologically intact function. For a subject suffering from cardiac arrest, concurrent administration of EPO with resuscitation but after the onset of the cardiac arrest facilitates the resuscitation. The mechanism by which EPO facilitates resuscitation from cardiac arrest involves preservation of left ventricular myocardial distensibility enabling hemodynamically more effective chest compression. Such hemodynamically more effective chest compression results in a higher coronary perfusion pressure leading to higher myocardial blood flow and consequently higher rates of return of spontaneous circulation. The hemodynamically more effective chest compression also enables shorting the duration of the resuscitation interval such that spontaneous circulation is restored earlier and with fewer additional resuscitation interventions. In addition, individuals who receive EPO during cardiac resuscitation and are successfully resuscitated have a higher likelihood of neurologically intact survival. This effects likely stems from shortening the duration of the resuscitation efforts and therefore shortening the duration of global ischemia associated with cardiac arrest and resuscitation and from beneficial tissue effects of EPO that manifest during the post-resuscitation phase such as better myocardial and hemodynamic function.

BACKGROUND OF THE INVENTION

It is estimated that approximately 330,000 individuals suffer an episode of sudden cardiac arrest every year in the United States. Yet, the percentage of individuals who are successfully resuscitated and leave the hospital alive with intact neurological function averages only 7% nationwide. Efforts to successfully restore life are formidably challenging. They require not only that cardiac activity be initially reestablished but that injury to vital organs be prevented or minimized. A closer examination of resuscitation statistics reveals that efficient emergency medical services (EMS) systems can initially restore cardiac activity in 30 to 40% of sudden cardiac arrest victims. Yet, nearly 40% die before admission to a hospital presumably from recurrent cardiac arrest or complications during transport. Of those admitted to a hospital, 60% die before discharge as a result of myocardial dysfunction, hypoxic brain damage, systemic inflammatory responses, intercurrent illnesses, or a combination thereof. Driving poor outcome is the severe injury that tissues suffer consequent to ischemia and reperfusion.

A cardiac arrest is the cessation of normal circulation of the blood due to failure of the ventricles of the heart to contract effectively resulting in the cessation of blood delivery to the whole body. As a consequence cells of the whole body suffer injury that result from oxygen starvation. Lack of oxygen supply to the brain causes victims to immediately lose consciousness and stop breathing. Cardiac arrest is different from a heart attack (myocardial infarction). In a cardiac arrest the heart suddenly stops beating. In a heart attack, blood flow to a region of the heart muscle is disrupted. That region of the heart muscle deprived of blood flow suffers injury which might lead to cell death if blood flow is not restored promptly. During a heart attack, only a part of the heart ceases to work properly; the rest of the heart muscle continues to work promoting blood flow albeit the total work produced by the heart may be sometimes diminished. However, heart attacks can sometimes lead to cardiac arrest in which the heart as whole stops beating and ceases to promote blood flow into the systemic circulation (as described above).

In apparently healthy adults, cardiac arrest is often precipitated by ventricular fibrillation. Ventricular fibrillation most often is associated with underlying coronary artery disease. In this setting, ventricular fibrillation may be the initial manifestation of a heart attack. However, ventricular fibrillation does not have to be associated with a heart attack, but can be associated with electrical abnormalities of the heart muscle originating in a region of the heart in which there is reduction of blood flow or disproportionate increase in oxygen demands in such region. Ventricular fibrillation can also be associated with the following: structural abnormalities of the heart—such as those caused by ischemic heart disease or by non-ischemic cardiomyopathies—that alters the normal propagation of electrical impulses creating areas in which chaotic electrical activity can originate and propagate through the rest of the heart muscle; associated with trauma to the heart; congenital or acquired abnormalities of ion channels that regulate the way in which the electrical impulse of the heart is initiated and propagated; the administration of drugs that can alter such ion channels; abnormalities in the chemical composition of the blood that can alter the way in which the electrical impulse of the heart is initiated and propagated; and abnormalities in the valves of the heart. Cardiac arrest can also occur without ventricular fibrillation, for example in cases in which the heart stops beating because of asystole in which there is no electrical impulses originating from the heart, or because of pulseless electrical activity in which electrical impulses originating from the heart are not effective to promote normal contraction of the heart muscle. Cardiac arrest caused by asystole or pulseless electrical activity is typically associated with conditions leading to severe curtailment of the amount of oxygen delivered to the heart muscle, which may be associated with respiratory failure or severe loss of circulating blood volume. Cardiac arrest caused by asystole or pulseless electrical activity can also be associated with existing cardiac disease, especially when severe heart failure has developed. However, asystole or pulseless electrical activity more commonly occurs after a period of untreated or ineffectively treated ventricular fibrillation. In this setting, the ventricular fibrillation activity gradually decreases and eventually ceases leading to asystole or pulseless electrical activity. This explains why individuals in whom cardiac arrest is precipitated by ventricular fibrillation, at the time of initial rhythm analysis asystole or pulseless electrical activity is present in more that 50% of the instances.

In children, cardiac arrest is more commonly caused by severe curtailment of oxygen delivery to the heart muscle, which may be associated with near-drowning or respiratory failure. However, children can also suffer cardiac arrest caused by ventricular fibrillation.

After onset of cardiac arrest, profound global myocardial ischemia develops. The ensuing resuscitation efforts promote flow through the ischemic myocardium, which—albeit obligatory for resuscitation—creates conditions for reperfusion injury. As a consequence several functional myocardial abnormalities develop during cardiac arrest and the resuscitation effort that in of itself can compromise the capability for reestablishing cardiac activity. These abnormalities include the progressive loss of left ventricular myocardial distensibility during cardiac resuscitation that manifests by left ventricular wall thickening with reductions in cavity size and which limits the ability of chest compression to promote forward blood flow. Early after return of spontaneous cardiac activity, there is prominent ventricular ectopic activity with frequent episodes of refibrillation. In addition, systolic and diastolic left ventricular function is reversibly impaired causing variable degrees of hemodynamic dysfunction. We have previously shown that these myocardial abnormalities can be ameliorated by inhibition of the sodium-hydrogen exchanger isoform-1 (NHE-1) using cariporide (Ayoub I M, Kolarova J D, Yi Z, Trevedi A, Deshmukh H, Lubell D L, Franz M R, Maldonado F A, Gazmuri R J. Sodium-hydrogen exchange inhibition during ventricular fibrillation: Beneficial effects on ischemic contracture, action potential duration, reperfusion arrhythmias, myocardial function, and resuscitability. *Circulation* 2003; 107:1804-1809; Gazmuri R J, Ayoub I M, Hoffner E, Kolarova J D. Successful ventricular defibrillation by the selective sodium-hydrogen exchanger isoform-1 inhibitor cariporide. *Circulation* 2001; 104:234-239; Gazmuri R J, Hoffner E, Kalcheim J, Ho H, Patel M, Ayoub I M, Epstein M, Kingston S, Han Y. Myocardial protection during ventricular fibrillation by reduction of proton-driven sarcolemmal sodium influx. *J Lab Clin Med* 2001; 137:43-55; Kolarova J D, Ayoub I M, Gazmuri R J. Kolarova J D, Ayoub I M, Gazmuri R J. Cariporide enables hemodynamically more effective chest compression by leftward shift of its flow-depth relationship. *Am J Physiol Heart Circ Physiol* 2005; 288:H2904-H2911; Kolarova J, Yi Z, Ayoub I M, Gazmuri R J. Cariporide potentiates the effects of epinephrine and vasopressin by nonvascular mechanisms during closed-chest resuscitation. *Chest* 2005; 127:1327-1334).

The present invention discloses that administration of the glycoprotein hormone EPO also serves to attenuate these myocardial abnormalities and favor improved resuscitation. EPO is a 30.4-kDa glycoprotein best known for its action on erythroid progenitor cells and regulation of circulating red cell mass. However, EPO also activates potent cell protective mechanisms during ischemia and reperfusion in a broad array of tissues, including the myocardium (Cai Z, Manalo D J, Wei G, Rodriguez E R, Fox-Talbot K, Lu H, Zweier J L, Semenza G E Hearts from rodents exposed to intermittent hypoxia or erythropoietin are protected against ischemia-reperfusion injury. *Circulation* 2003; 108:79-85; Calvillo L, Latini R, Kajstura J, Len A, Anversa P, Ghezzi P, Salio M, Cerami A, Brines M. Recombinant human erythropoietin protects the myocardium from ischemia-reperfusion injury and promotes beneficial remodeling. *Proc Natl Acad Sci USA* 2003; 100: 4802-4806; Moon C, Krawczyk M, Ahn D, Ahmet I, Paik D, Lakatta E G, Talan M I. Erythropoietin reduces myocardial infarction and left ventricular functional decline after coronary artery ligation in rats. *Proc Natl Acad Sci USA* 2003; 100:11612-11617; Parsa C J, Matsumoto A, Kim J, Riel R U, Pascal L S, Walton G B, Thompson R B, Petrofski J A, Annex B H, Stamler J S, Koch W J. A novel protective effect of erythropoietin in the infarcted heart. *J Clin Invest* 2003; 112: 999-1007; Tramontano A F, Muniyappa R, Black A D, Blendea M C, Cohen I, Deng L, Sowers J R, Cutaia M V, El Sherif N. Erythropoietin protects cardiac myocytes from hypoxia-induced apoptosis through an Akt-dependent pathway. *Biochem Biophys Res Commun* 2003; 308:990-994; Cai Z, Semenza G L. Phosphatidylinositol-3-kinase signaling is required for erythropoietin-mediated acute protection against myocardial ischemia/reperfusion injury. *Circulation* 2004; 109:2050-2053; Lipsic E, van der M P, Henning R H, Suurmeijer A J, Boddeus K M, van Veldhuisen D J, van Gilst W H, Schoemaker R G. Timing of erythropoietin treatment for cardioprotection in ischemia/reperfusion. *J Cardiovasc Pharmacol* 2004; 44:473-479; Parsa C J, Kim J, Riel R U, Pascal L S, Thompson R B, Petrofski J A, Matsumoto A, Stamler J S, Koch W J. Cardioprotective effects of erythropoietin in the reperfused ischemic heart: a potential role for cardiac fibroblasts. *J Biol Chem* 2004; 279:20655-20662; Wright G L, Hanlon P, Amin K, Steenbergen C, Murphy E, Arcasoy M O. Erythropoietin receptor expression in adult rat cardiomyocytes is associated with an acute cardioprotective effect for recombinant erythropoietin during ischemia-reperfusion injury. *FASEB J* 2004; 18:1031-1033; Namiuchi S, Kagaya Y, Ohta J, Shiba N, Sugi M, Oikawa M, Kunii H, Yamao H, Komatsu N, Yui M, Tada H, Sakuma M, Watanabe J, Ichihara T, Shirato K. High serum erythropoietin level is associated with smaller infarct size in patients with acute myocardial infarction who undergo successful primary percutaneous coronary intervention. *J Am Coll Cardiol* 2005; 45:1406-1412). These protective effects are mediated through genomic and non-genomic mechanisms; with the non-genomic mechanisms being particular relevant to acute protection (Bullard A J, Govewalla P, Yellon D M. Erythropoietin protects the myocardium against reperfusion injury in vitro and in vivo. *Basic Res Cardiol* 2005; 100:397-403; Rafiee P, Shi Y, Su J, Pritchard K A, Jr., Tweddell J S, Baker J E. Erythropoietin protects the infant heart against ischemia-reperfusion injury by triggering multiple signaling pathways. *Basic Res Cardiol* 2005; 100:187-197; Nishihara M, Miura T, Miki T, Sakamoto J, Tanno M, Kobayashi H, Ikeda Y, Ohori K, Takahashi A, Shimamoto K. Erythropoietin affords additional cardioprotection to preconditioned hearts by enhanced phosphorylation of glycogen synthase kinase-3 beta. *Am J Physiol Heart Circ Physiol* 2006; 291:H748-H755).

EPO has been traditionally viewed as a primary regulator of red blood cell production (Graber S E, Krantz S B. EPO and the control of red cell production. *Annu Rev Med* 1978; 29:51-66). Yet, recent studies demonstrate the EPO also exerts protective effects on the myocardium in the setting of ischemia and reperfusion injury (Cai Z, Manalo D J, Wei G, Rodriguez E R, Fox-Talbot K, Lu H, Zweier J L, Semenza G L. Hearts from rodents exposed to intermittent hypoxia or EPO are protected against ischemia-reperfusion injury (*Circulation* 2003; 108:79-85; Calvillo L, Latini R, Kajstura J, Leri A, Anversa P, Ghezzi P, Salio M, Cerami A, Brines M. Recombinant human EPO protects the myocardium from ischemia-reperfusion injury and promotes beneficial remodeling. *Proc Natl Acad Sci USA* 2003; 100:4802-4806; Tramontano A F, Muniyappa R, Black A D, Blendea M C, Cohen I, Deng L, Sowers J R, Cutaia M V, El Sherif N. EPO protects cardiac myocytes from hypoxia-induced apoptosis through an Akt-dependent pathway. *Biochem Biophys Res Commun* 2003; 308:990-994; Cai Z, Semenza G L. Phosphatidylinositol-3-kinase signaling is required for EPO-mediated acute protection against myocardial ischemia/reperfusion injury. *Circulation* 2004; 109:2050-2053; Lipsic E, van der Meer P, Henning R H, Suurmeijer A J H, Boddeus K M, van Veldhuisen D J, van Gilst W H, Schoemaker R G. Timing of EPO treatment for cardioprotection in ischemia/reperfusion; United States Patent Application Pub. No. 2004/0009908A1;

United States Patent Application Pub. No. 2004/0198663A1; United States Patent Application Pub. No. 2005/0075287; International Patent Application WO 03/057242; International Patent Application No. WO 2004/00464). In a rat model of myocardial infarction caused by left anterior descending coronary artery (LAD) occlusion and reperfusion, administration of recombinant human erythropoietin (rhEPO) attenuated post infarct deterioration in hemodynamic function by reduction of cardiomyocyte loss, attenuated the reactive hypertrophy of surviving cardiomyocytes, and also prevented apoptosis (Moon C, Krawczyk M, Ahn D, Ahmet I, Paik D, Lakatta E G, Talan M I. *EPO reduces myocardial infarction and left ventricular functional decline after coronary artery ligation in rats. Proc Natl Acad Sci USA* 2003; 100:11612-11617).

These and other aspects and attributes of the present invention will be discussed with reference to the following drawings and accompanying specification.

BRIEF SUMMARY OF THE INVENTION

In an embodiment, the present invention discloses a method for facilitating cardiac resuscitation in a mammalian subject suffering from cardiac arrest comprising administration of an effective amount of erythropoietin (EPO), or its derivative, or a functional fragment thereof, to the subject concurrent with cardiac resuscitation and after the onset of cardiac arrest. In a preferred embodiment, the mammalian subject is human. In another preferred embodiment, the EPO is a recombinant human EPO (rhEPO). The effective amount of EPO can be from about 200 IU/kg to about 6,000 IU/kg, and preferably 5,000 IU/kg.

The method for cardiac resuscitation in the present invention can be manual, mechanical, electrical, chemical, or a combination thereof. The cardiac resuscitation can also be performed with a closed chest or with an open chest.

The EPO can be administered by a route selected from, but not limited to, intravenous (IV), intraarterial (IA), intraperitoneal (IP), intracardiac (IC), and intraosseous (IO). The administration can be bolus or continuous.

The EPO, or its derivative, or a functional fragment thereof, can be administered just immediately before cardiac resuscitation, at the beginning of the cardiac resuscitation, or during cardiac resuscitation. In an embodiment, the cardiac arrest is due to ventricular fibrillation.

DETAILED DESCRIPTION OF THE INVENTION

Figure 1:
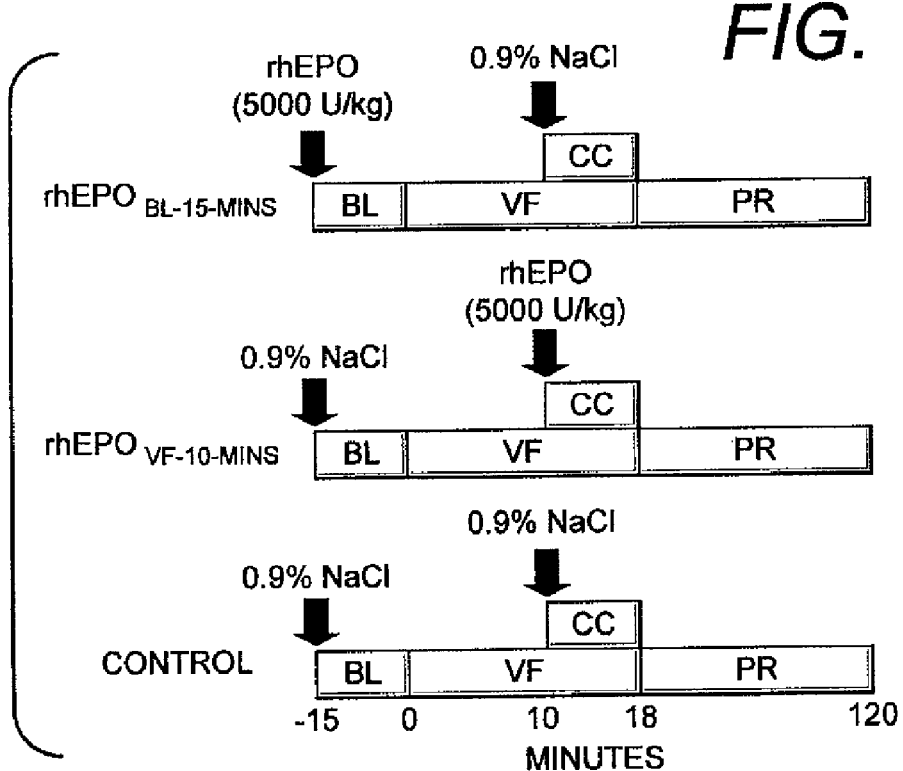
FIG. 1 is a schematic diagram showing the study design for the present invention using a rat model of ventricular fibrillation (BL=baseline, VF=ventricular fibrillation, CC=chess compression, and PR=post-resuscitation). With the investigators blind to the assignment, rats were randomized to receive a right atrial bolus of rhEPO (5000 IU/kg) at baseline 15 minutes before induction of VF (rhEPO$_{BL-15-min}$), at 10 minutes of VF immediately before starting chest compression (rhEPO$_{VF\ 10-min}$), or 0.9% NaCl solution (control)

While this invention is susceptible of embodiment in many different forms, there is shown in the drawings, and will be described herein in detail, specific embodiments thereof with the understanding that the present disclosure is to be considered as an exemplification of the principles of the invention and is not intended to limit the invention to the specific embodiments illustrated.

The present invention relates generally to the use of EPO to facilitate resuscitation from cardiac arrest. For a mammalian subject suffering from cardiac arrest, concurrent administration of EPO with resuscitation facilitates the resuscitation. Administration of EPO serves to attenuate myocardial abnormalities caused by cardiac arrest and the resuscitation effort and favors improved resuscitation outcomes. Without being bound by any one or more specific theories, the improved resuscitation outcomes may be explained by one or more of the following hypotheses: 1) administration of EPO during cardiac arrest and resuscitation prevents reductions in left ventricular myocardial distensibility enabling chest compression or any other mechanism intended to artificially eject blood from the left ventricular cavity to be hemodynamically more effective—i.e., enabling ejection of a larger amount of blood—leading to a higher coronary perfusion pressure levels that increases the rate of and shortens the time to successful restoration of cardiac activity with return of effective spontaneous circulation; 2) administration of EPO during cardiac arrest and resuscitation ameliorates post-resuscitation myocardial dysfunction; 3) administration of EPO during cardiac arrest and resuscitation and improves survival with intact neurologically function; and 4) the treatment effect of EPO increases as the severity of ischemic injury increases (e.g., as a result of prolonging the duration of untreated ventricular fibrillation).

To test these hypotheses, studies were initially conducted in a rat model of ventricular fibrillation and subsequently in a cohort of human subjects suffering out-of-hospital cardiac arrest. Both studies are described in detail below.

Example One

Rat Model Study Design

Studies were conducted in a rat model of ventricular fibrillation and closed-chest resuscitation to assess the effects of the interventions (in this case, the intervention is the administration of EPO) on the hemodynamic efficacy of chest compression, resuscitability, post-resuscitation ectopic activity, post-resuscitation myocardial function, and short-term survival.

The ventricular fibrillation model is significantly different than the coronary occlusion models used by others in studying cardioprotection from ischemia and reperfusion injury. In the ventricular fibrillation model used in the present disclosure, ventricular fibrillation is induced by delivering a 60-Hz alternating current to the right ventricular endocardium. This, results in cessation of the organized activity of the heart required for effective work as a pump leading to cessation of total body blood flow. Moreover, the myocardial ischemia induced by ventricular fibrillation is global (throughout the entire heart muscle). The ventricular fibrillation model is best suited for studying cardiac arrest. In the occlusion model, a coronary artery is ligated to reduce or stop blood flow to the heart to induce myocardial infarction (MI). Ischemia induced by occlusion of the coronary artery is occurring in only part of the heart, not the entire heart muscle. The occlusion model is best suited for studying acute coronary syndromes. In the ventricular fibrillation model, the heart suddenly stops beating. This is different from a heart attack in the occlusion model in which blood flow to the heart is disrupted to the point that part of the heart muscle dies but the rest continues to function promoting systemic blood flow. Coronary occlusion, however, can sometimes lead to cardiac arrest. In the ventricular fibrillation model the heart suffers intense ischemia because in addition to cessation of blood supply, the metabolic needs of the heart muscle are increased by the fibrillatory activity. In addition, because the duration of the episode of myocardial ischemia is much shorter in the ventricular fibrillation model than in the occlusion model (i.e., 5, 8, or 10 minutes vs 30, 45, or 60 minutes) before reperfusion, the main abnormality in the ventricular fibrillation model is that of dysfunction whereas in the coronary occlusion model the main abnormality is that of cell death. The main therapeutic goal in the ventricular fibrillation model is the prevention of cell dysfunction; whereas the main therapeutic goal in the coronary occlusion model is the prevention of cell death. In addition, the ventricular fibrillation model is accompanied by whole body ischemia and responses that are unique to the cardiac arrest setting that can also influence the heart. Thus, the same benefit produced by EPO in the heart may apply to other organs including the brain during cardiac arrest.

The rat study design is shown schematically in FIG. 1. Ventricular fibrillation was left untreated for 10 minutes. Chest compression was then started and defibrillation attempted 8 minutes later (after 18 minutes of ventricular fibrillation). Three groups of ten rats each were randomized to receive (a) rhEPO (EPOGEN®, Amgen Inc., Thousand Oaks, Calif., USA) in bolus dose of 5000 IU/kg into the right atrium at 15 minutes before induction of ventricular fibrillation and equal volume of 0.9% NaCl at 10 minutes of untreated ventricular fibrillation immediately before start of chest compression ($rhEPO_{BL-15-min}$), (b) 0.9% NaCl at 15 minutes before induction of ventricular fibrillation and rhEPO 5000 IU/kg at 10 minutes of untreated ventricular fibrillation immediately before starting chest compression ($rhEPO_{BL\ 10-min}$), and (c) 0.9% NaCl at 15 minutes before induction of ventricular fibrillation and at 10 minutes of untreated ventricular fibrillation (Control). The investigators were blind to the treatment assignment.

The EPO dose was chosen empirically based on previous reports in which doses ranging between 1000 IU/kg to 5000 IU/kg were used intraperitoneally (Cai Z, Manalo D J, Wei G, Rodriguez E R, Fox-Talbot K, Lu H, Zweier J L, Semenza G L. Hearts from rodents exposed to intermittent hypoxia or EPO are protected against ischemia-reperfusion injury. *Circulation* 2003; 108:79-85; Calvillo L, Latini R, Kajstura J, Leri A, Anversa P, Ghezzi P, Salio M, Cerami A, Brines M. Recombinant human EPO protects the myocardium from ischemia-reperfusion injury and promotes beneficial remodeling. *Proc Natl Acad Sci USA* 2003; 100:4802-4806; Tramontano A F, Muniyappa R, Black A D, Blendea M C, Cohen I, Deng L, Sowers J R, Cutaia M V, El Sherif N. EPO protects cardiac myocytes from hypoxia-induced apoptosis through an Akt-dependent pathway. *Biochem Biophys Res Commun* 2003; 308:990-994; Moon C, Krawczyk M, Ahn D, Ahmet I, Paik D, Lakatta E G, Talan M I. EPO reduces myocardial infarction and left ventricular functional decline after coronary artery ligation in rats. *Proc Natl Acad Sci USA* 2003; 100:11612-11617), one study in which a dose of 300 IU/kg was used intravenously (Abdelrahman M, Sharples E J, McDonald M C, Collin M, Patel N S, Yaqoob M M, Thiemermann C. EPO attenuates the tissue injury associated with hemorrhagic shock and myocardial ischemia. *Shock* 2004; 22:63-69), and one study in an isolated rat heart preparation in which the heart was exposed to 10 U/ml (Wright G L, Hanlon P, Amin K, Steenbergen C, Murphy E, Arcasoy M O. EPO receptor expression in adult rat cardiomyocytes is associated with an acute cardioprotective effect for recombinant EPO during ischemia-reperfusion injury. *FASEB J* 2004; 18:1031-1033). Given that the volume of distribution of EPO has been reported to range between 0.021 L/kg to 0.61 L/kg (Lim V S, DeGowin R L, Zavala D, Kirchner P T, Abels R, Perry P, Fangman J. Recombinant human EPO treatment in pre-dialysis patients. A double-blind placebo-controlled trial. *Ann Intern Med* 1989; 110:108-114; Macdougall I C, Roberts D E, Neubert P, Dharmasena A D, Coles G A, Williams J D. Pharmacokinetics of recombinant human EPO in patients on continuous ambulatory peritoneal dialysis. *Lancet* 1989; 1:425-427), in a 500 g rat, the volume of distribution would range from ≅10 to 300 ml. Thus, to attain a plasma concentration of 10 IU/ml (as in the isolated rat heart study), the total amount of EPO required would range from about 100 IU to about 3000 IU corresponding to a single dose of about 200 IU/kg to about 6000 IU/kg. Given no expected adverse effects, we chose the upper range and selected a dose of 5000 IU/kg. Yet, a few pilot studies (i.e., 2 rats) were conducted to assess for hemodynamic effects during spontaneous circulation in our model. The formulation of EPO used in these experiments was 4000 IU/ml. Thus, the volume of EPO and 0.9% NaCl (control) to be administered was 1.25 ml/kg. EPO was kept refrigerated at 4° C. and warmed to room temperature before use. This dose of EPO would not be expected to increase the hematocrit but to have an effect during the episode of resuscitation and the subsequent post-resuscitation interval. During an observation period of 120 minutes post-resuscitation, no change in hematocrit relative to control rats occurred.

Animal Preparation

Sprague-Dawley rats (450-550 g) were anesthetized by intraperitoneal injection of sodium pentobarbital (45 mg/kg) and supplemented with 10 mg/kg at 30-minute intervals. Core temperature was maintained between 36.5° C. and 37.5° C. using an infrared heating lamp. A 5 F catheter was orally advanced into the trachea and used subsequently for mechanical ventilation. Proper placement was verified with an infrared $CO_2$ analyzer (CO2SMO model 7100, Novametrix Medical Systems, Inc). A conventional lead II electrocardiogram was recorded through subcutaneous needles. Through the left femoral vein, a PE50 catheter was advanced into the right atrium for measurement of right atrial pressure. Through the right femoral artery, a PE50 catheter was advanced into the abdominal aorta for aortic pressure measurements and blood sampling. Through the left femoral artery, a thermocouple microprobe (IT-18, Physitemp) was advanced to measure cardiac output by thermodilution technique. Through the left jugular vein, a PE50 catheter was advanced into the right atrium for bolus injection of 0.9% NaCl for cardiac output measurement. In addition, a precurved guide was advanced into the right atrium through the right jugular vein and was used for induction of ventricular fibrillation.

Experimental Protocol

Ventricular fibrillation was induced by delivering a 60-Hz alternating current to the right ventricular endocardium and left untreated for a predetermined interval. Chest compression was then initiated using an electronically controlled and pneumatically driven (50 PSI) chest compressor (CJ-80623, CJ Enterprises) programmed to deliver 200 compressions per minute. The depth of compression was adjusted within the initial two minutes to attain an aortic diastolic pressure between 26 and 28 mmHg and thus secure a coronary perfusion pressure above the resuscitability threshold of 20 mmHg in rats. The location and depth of compression were adjusted if required to secure that the coronary perfusion pressure remained within the target range throughout chest compression. The depth of compression was continuously measured using a displacement transducer. Positive pressure ventilation was concomitantly provided with a volume controlled ventilator (model 683, Harvard Apparatus) programmed to deliver 25 unsynchronized breaths per minute using 100% oxygen. Defibrillation was attempted after 8 minutes of chest compression by delivering a maximum of two 3-J transthoracic shocks using a biphasic waveform defibrillator (Smart Biphasic Heartstream XL M4735A, Agilent Technologies). If ventricular fibrillation persisted or an organized rhythm with a mean aortic pressure of $\leq 25$ mmHg ensued, chest compression was resumed for 30 seconds. The defibrillation-compression cycle was repeated for up to three additional times, increasing the energy of individual shocks (if ventricular fibrillation persisted) to 5-J and then to 7-J for the last two cycles. Successful cardiac resuscitation was defined as the return of an organized electrical activity with a mean aortic pressure $\geq 60$ mmHg for $\geq 5$ minutes. Successfully resuscitated rats were monitored for 120 minutes. At the end of 120 minutes euthanasia was performed by intravenous injection of sodium pentobarbital (150 mg/kg). These procedures were consistent with the recommendations of the Panel on Euthanasia of the American Veterinarian Medical Association. Autopsy was performed opening the thoracic and abdominal cavity. Organs were inspected for evidence of traumatic injury related to vascular catheterization and chest compression.

Rat Study Measurements and Data Analysis

Analog signals were processed using BIOPAC signal-conditioners (BIOPAC Systems, Inc) and digitized at 250 scans/second using a 16-bit data acquisition board (AT-MIO-16XE-50, National Instruments). The signals were displayed, stored, and analyzed using programs written for Lab VIEW 4.01 (National Instruments). Vascular pressures were measured using fluid-filled catheters and conventional pressure transducers referenced to mid-chest level. Coronary perfusion pressure was calculated as the aortic minus the right atrial pressure at the end of chest relaxation during chest compression. Cardiac output was measured after bolus injection of 200-µL of 0.9% NaCl at room temperature into the right atrium. The dilution curves were analyzed using custom-developed LabVIEW-based software.

The data were analyzed using SigmaStat™ for Windows. ANOVA with multicomparison procedures used to test for differences among groups at specific time intervals. Comparable non-parametric tests were substituted when tests for normality and equal variance failed. A p-value of <0.05 was considered statistically significant.

Rat Study Results

Figure 2:
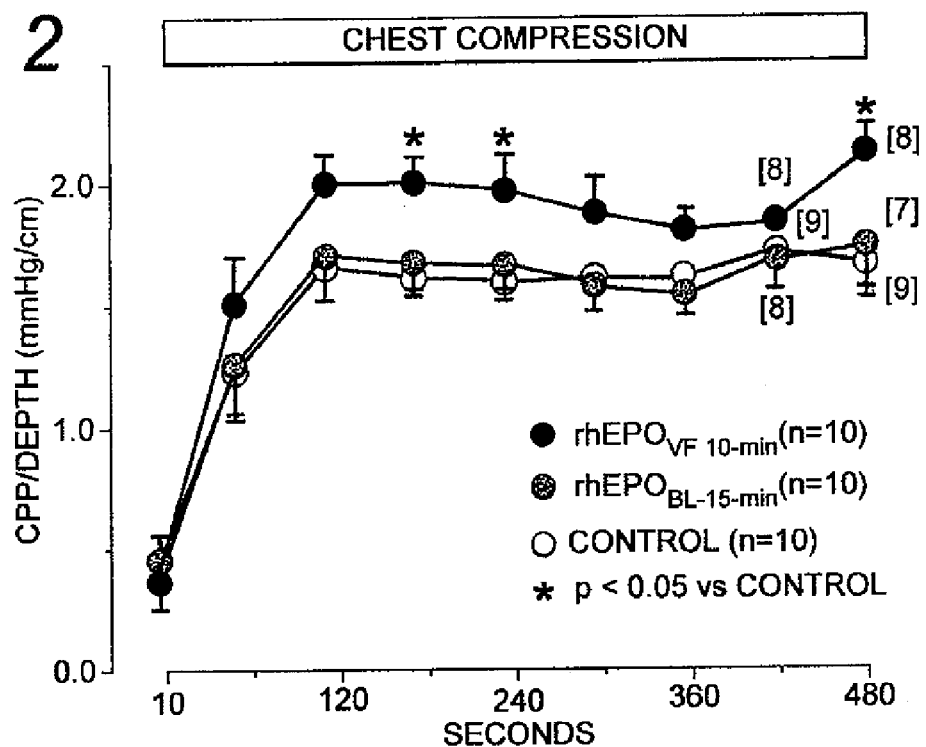
FIG. 2 is a graphical representation of the ratio between coronary perfusion pressure (CPP) and depth of compression during closed-chest resuscitation in rats treated with human recombinant EPO (rhEPO) as shown in FIG. 1 and described below in the text. Rats that received rhEPO had a significantly higher CPP/depth ratio during chest compression indicative that rhEPO prevented reductions in left ventricular myocardial distensibility and thereby enhanced the hemodynamic efficacy of closed-chest resuscitation.

The rat study results are summarized in FIGS. 2, 3, 4, and 5. EPO given coincident with the beginning of chest compression after 10 minutes of untreated ventricular fibrillation—but not before inducing ventricular fibrillation—promoted hemodynamically more effective chest compression such that the ratio between the coronary perfusion pressure and the depth of compression (CPP/Depth) averaged during the interval of chest compression was 2.0±0.3 mmHg/mm in $rhEPO_{VF\ 10\text{-}min}$, 1.6±0.2 mmHg/mm in $rhEPO_{BL\text{-}15\text{-}min}$, and 1.6±0.3 mmHg/mm in the control group (p<0.05 $rhEPO_{VF\ 10\text{-}min}$ vs $rhEPO_{BL\text{-}15\text{-}min}$ and vs control). This difference represented a 25% improvement in the hemodynamic efficacy of chest compression with EPO given at the beginning of chest compression. In FIG. 2, the CPP/Depth ratio is depicted throughout chest compression. The possibility that the higher CPP/Depth ratio resulted from a vasopressor effect of EPO during chest compression seemed unlikely; baseline hemodynamic measurements in the group of rats that received EPO 15 minutes before induction of ventricular fibrillation ($rhEPO_{BL\text{-}15\text{-}min}$) demonstrated a statistically borderline decrease (not increase) in systemic vascular resistance from 1.092±0.147 to 1.010±0.133 mm Hg/mL/min/kg (P=0.077 by paired t-test).

Figure 3:
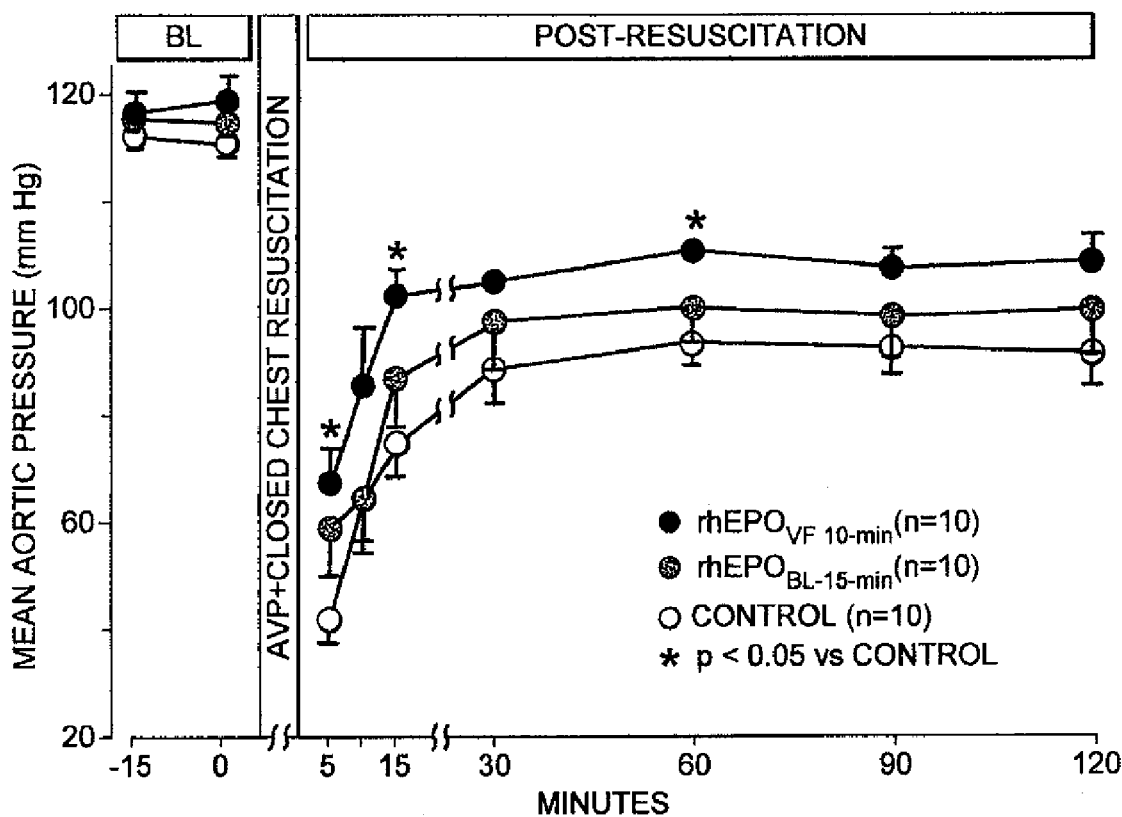
FIG. 3 is a graphical representation of the mean aortic pressure after return of spontaneous circulation (ROSC) in rats treated with rhEPO as described in the text.
Figure 4:
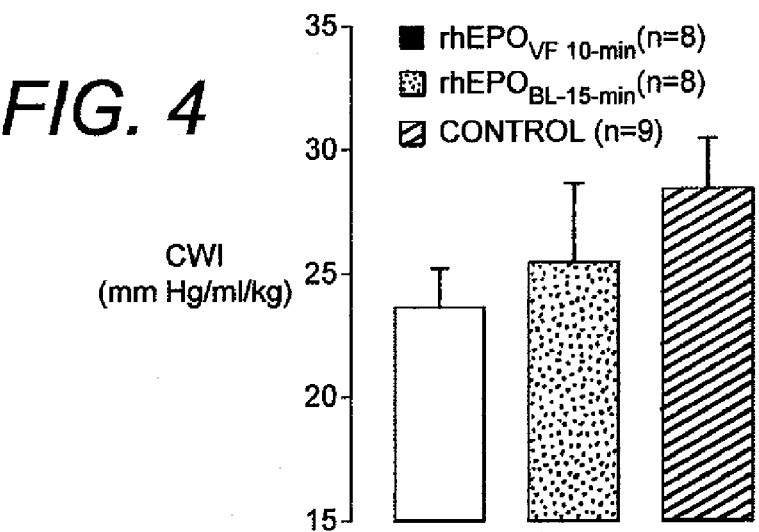
FIG. 4 is a graphical representation of the cardiac work index (CWI) averaged from post-resuscitation minute 10 to post-resuscitation minute 120 in rats treated with rhEPO. CWI was calculated as the difference between the mean aortic and mean right atrial pressure times the stroke volume index.

Post-resuscitation, $rhEPO_{VF\ 10\text{-}min}$ rats had significantly higher mean aortic pressure than control rats (FIG. 3). Cardiac work calculated as the difference between the mean aortic and mean right atrial pressure times the stroke volume index was higher in $rhEPO_{VF\ 10\text{-}min}$ rats than in $rhEPO_{BL\text{-}15\text{-}min}$ rat and than in control rats (FIG. 4). This is consistent with reports by other investigators in similar animal models of cardiac arrest and resuscitation demonstrating that administration of EPO before inducing cardiac arrest or shortly after restoration of cardiac activity improves post-resuscitation myocardial function (Huang C H, Hsu C Y, Chen H W, Tsai M S, Cheng H J, Chang C H, Lee Y T, and Chen W J. Erythropoietin improves postresuscitation myocardial dysfunction and survival in the asphyxia-induced cardiac arrest model. *Shock* 2007; 28:53-8; Huang C H, Hsu CY, Tsai M S, Wang T D, Chang W T, and Chen W J. Cardioprotective effects of erythropoietin on postresuscitation myocardial dysfunction in appropriate therapeutic windows. *Crit. Care Med* 2008; 36:S467-S473).

Figure 5:
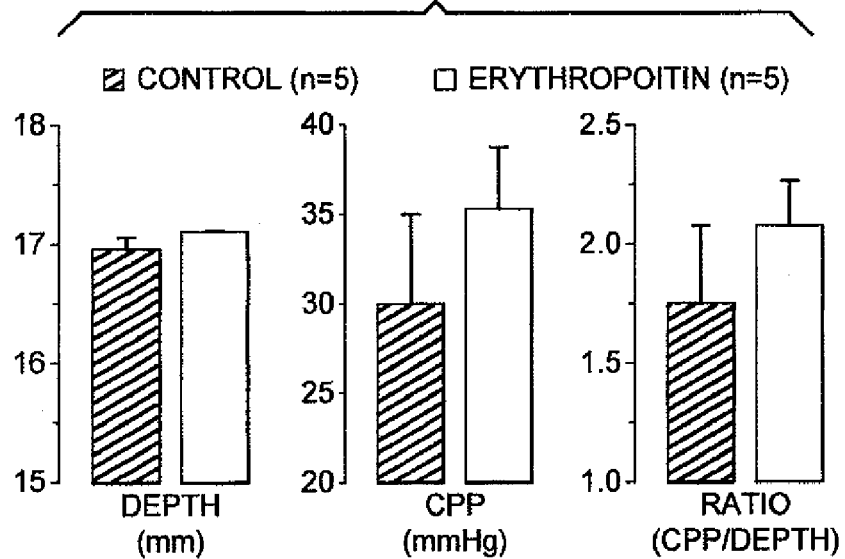
FIG. 5 is a graphical representation of the depth of chest compression (Depth), the coronary perfusion pressure (CPP), and the ratio between CPP and Depth (CPP/Depth) in a separate series of experiment using the rat model of ventricular fibrillation and closed-chest resuscitation described above. Measurements are shown at 7 minutes of chest compression immediately before attempting restoration of spontaneous cardiac activity by delivery of an electrical shock.

Additional observations were made using the same rat model of ventricular fibrillation and closed-chest resuscitation but applying a protocol in which the depth of chest compression during resuscitation was increased to 17 mm, which is the maximum level that is feasible in the rat model without causing traumatic injury to intrathoracic organs. This protocol was clinically more relevant enabling assessing the effects of EPO after maximizing the effects of chest compression. Under these experimental conditions 5,000 IU/kg of EPO given at the beginning of chest compression also prompted hemodynamically more effective chest compression yielding a coronary perfusion pressure approximately 5 mmHg higher than in control rats (FIG. 5). Such difference would be clinically relevant given that small increments in coronary perfusion pressure have marked effects on cardiac resuscitability (Paradis N A, Martin G B, Rivers E P, Goetting M G, Appleton T J, Feingold M, and Nowak R M. Coronary perfusion pressure and the return of spontaneous circulation in human cardiopulmonary resuscitation. *JAMA* 1990; 263: 1106-13).

We have reported similar effects associated with other interventions targeting ischemia and reperfusion injury, demonstrating that preservation of left ventricular myocardial distensibility yields higher left ventricular volumes for a given left ventricular pressure during resuscitation before each chest compression (Kolarova J D, Ayoub I M, Gazmuri R J. Cariporide enables hemodynamically more effective chest compression by leftward shift of its flow-depth relationship. *Am J Physiol Heart Circ Physiol* 2005; 288:H2904-H2911; Gazmuri R J, Ayoub I M, Hoffner E, Kolarova J D. Successful ventricular defibrillation by the selective sodium-hydrogen exchanger isoform-1 inhibitor cariporide. *Circulation* 2001; 104:234-239; Ayoub I M, Kolarova J D, Yi Z, Trevedi A, Deshmukh H, Lubell D L, Franz M R, Maldonado F A, Gazmuri R J. Sodium-hydrogen exchange inhibition during ventricular fibrillation: Beneficial effects on ischemic contracture, action potential duration, reperfusion arrhythmias, myocardial function, and resuscitability. *Circulation* 2003; 107:1804-1809; Ayoub I M, Kolarova J, Kantola R, Radhakrishnan J, Gazmuri R J. Zoniporide preserves left ventricular compliance during ventricular fibrillation and minimizes post-resuscitation myocardial dysfunction through benefits on energy metabolism. *Crit. Care Med* 2007; 35:2329-2336).

Example Two

Human Model Study Design

The preceding observations in rats prompted a study in humans aimed at determining whether EPO administered during cardiopulmonary resuscitation (CPR) in victims of out-of-hospital cardiac arrest could improve resuscitation outcomes (Grmec S, Strnad M, Kupnik D, Sinkovic A, and Gazmuri R J. Erythropoietin facilitates the return of spontaneous circulation and survival in victims of out-of-hospital cardiac arrest. *Resuscitation* 2009; 80:631-7). The study design took into consideration key observations made in the rat experiments. Accordingly, EPO was administered early during the resuscitation effort and end-tidal $PCO_2$ ($P_{ET}CO_2$) was measured to estimate the hemodynamic efficacy of chest compression. The human study was conducted in the city of Maribor, Slovenia by a physician-led prehospital resuscitation team.

The human study was approved by the Ethical Board of the Ministry of Health of the Republic of Slovenia, granting waiver of the informed consent. Patients who regained consciousness—or their relatives—were informed of the study after enrollment whenever possible. The human study was conducted in the city of Maribor and adjacent rural areas encompassing a population of approximately 200,000 inhabitants spread over and area of about 780 $km^2$. The Centre for Emergency Medicine in Maribor hosts the Maribor EMS system, which is accessed through a single emergency number (i.e., 112). The system includes two prehospital emergency teams with advanced life support (ALS) capability, two basic life support (BLS) teams, and during daytime—from April to October—a rescuer on a motorcycle.

Each ALS team is comprised of one emergency physician and two additional personnel who are either registered nurses, medical technicians, or a combination; all with training in advanced cardiac life support. Each BLS team is comprised of two nurses or registered nurses and the motorcycle rescuer who is a nurse or a registered nurse, all with BLS training able to provide electrical defibrillation, chest compressions, ventilation, and oxygenation before arrival of the ALS team.

Once an emergency call is received (by dialing 112) an ALS team is dispatched to the scene. If the two ALS teams are responding to other emergencies, a BLS team is dispatched instead pending availability of one of the two ALS team. When available, the motorcycle rescuer is also dispatched typically arriving to the scene before the BLS or ALS team. Resuscitation of the cardiac arrest victims is initiated by the rescuer(s) who first arrive to the scene, using regionally developed protocols that incorporate ILCOR 2005 recommendations as described below.

Patients with ages ranging between 18 and 80 years old and who had non-traumatic normothermic out-of-hospital cardiac arrest were considered for inclusion in the study. Patients were excluded if they had terminal illness; cardiac arrest secondary to trauma, drowning, or hanging; had severe hypothermia (<30° C.); or regained spontaneous circulation before administration of a vasopressor agent.

Resuscitation Protocol

The ALS team initiated the resuscitation effort if they arrived at the scene first or continued ongoing efforts initiated by the BLS team. The ALS team placed an endotracheal tube—verifying proper position by capnography—and initiated positive pressure ventilation with a tidal volume of about 6 ml/kg delivered at 10 times per minute. The ALS team also established intravenous access through an external jugular vein or a hand vein typically within 30 seconds. The access was used to administer EPO (beta-epoetin as described below) or 0.9% NaCl as control solution—contingent on the study group—followed by 250 ml of 7.2% NaCl in 6% hydroxyethyl starch (HyperHaes® solution, Fresenius Kabi, Germany, GmbH) and other resuscitation drugs. Additional fluid, including 6% hydroxyethyl starch and 0.9% NaCl, was given at the discretion of the rescuers.

The cardiac rhythm and peripheral pulses were checked every two minutes. If ventricular fibrillation or ventricular tachycardia was present, a single 150-J biphasic waveform electrical shock was delivered and chest compressions resumed for another 2 minutes before re-assessing rhythm and pulse. If the patient remained in ventricular fibrillation or ventricular tachycardia after the second defibrillation attempt or if the patient had pulseless electrical activity or asystole as the presenting rhythm, an intravenous bolus of vasopressin (40 IU) was given followed by boluses of epinephrine (1 mg) every four minutes. For shock resistance ventricular fibrillation or ventricular tachycardia, 300 mg of amiodarone was given between the third and fourth electrical shock. For pulseless electrical activity or asystole 3 mg of atropine and about 5 mg/kg of theophylline were given.

Study Drug

Patients assigned to EPO received 90,000 IU of beta-epoetin (3 vials of NeoRecormon 30,000 IU each, 1.8 ml total, Hoffman La Roche) as a bolus through the external jugular vein or a hand vein within 1 or 2 minutes after starting chest compressions followed by a 10-ml bolus of 0.9% NaCl. Beta-epoetin was kept refrigerated between 2° C. and 8° C. in the ambulance until immediately before use. In every instance the study drug was given before any other drug.

Post-Resuscitation Care

Patients who had return of spontaneous circulation in the field were started on 0.9% NaCl solution cooled at 4° C. (30 ml/kg infused at 100 ml/min) and given 0.08-0.10 mg/kg of vecuronium bromide (Norcuron®, Organon) to initiate hypothermia while in route to the hospital. Hemodynamic stability was secured if needed by administering dopamine (5-10 μg/kg/min) for persistent hypotension (systolic blood pressure <90 mmHg), dobutamine (2.5-20.0 mg/kg/min) for suspected cardiogenic shock based on electrocardiographic findings and persistent hypotension, or norepinephrine (8-12 μg/kg/min) if systolic blood pressure remained <70 mmHg despite the preceding measures.

Patients were directly admitted to the Intensive Care Unit (ICU) at the University Clinical Center in Maribor and cooled to a core temperature between 32° C. and 34° C. by external means until they regained consciousness or had completed 24 hours. Patients with ST-segment elevation myocardial infarction had percutaneous coronary interventions. Inotropic and vasopressor agents were infused guided by hemodynamic monitoring using a pulmonary artery catheter and transthoracic echocardiography. The ICU team was composed of internal medicine physicians with subspecialty training in critical care medicine and managed the patients unaware of the treatment assignment.

The study was designed to test the null hypothesis that resuscitation outcomes do not differ between victims of out-of-hospital cardiac arrest who receive EPO and those who do not receive EPO during cardiopulmonary resuscitation.

Resuscitation Outcomes

The primary outcome was ICU admission. The secondary outcomes were return of spontaneous circulation in the field, survival at 24 hours, and survival at hospital discharge.

Study Groups

The study was originally designed as prospective and randomized. However, disruption in the supply of EPO (because of financial constraints), prompted investigators to administer EPO or 0.9% NaCl based on availability, allocating 24 patients to EPO and 30 to 0.9% NaCl between April 2007 and May 2008. The control group for this initial series was designated as concurrent controls.

Post-hoc, a second control group of 48 patients was selected by calculating propensity scores from a group of 126 patients who had out-of-hospital cardiac arrest between January 2006 and March 2007 and were subjected to the same resuscitation protocol. Propensity scores can be used to estimate the likelihood that a subject would have received treatment (i.e., EPO) based on pretreatment characteristics (covariates). Propensity scores (range, 0-1) are frequently calculated by multiple logistic regression where the dependent variable is the treatment and the independent variables are the pre-treatment variables (covariates), enabling multiple covariates to be simultaneously reduced to a single variable which is the propensity score (Kurth T, Walker A M, Glynn R J, Chan K A, Gaziano J M, Berger K, Robins J M. Results of multivariable logistic regression, propensity matching, propensity adjustment, and propensity-based weighting under conditions of nonuniform effect. *Am J Epidemiol* 2006; 163:262-270; D'Agostino R B, Jr. Propensity scores in cardiovascular research. *Circulation* 2007; 115: 2340-2343). For the present study, propensity scores were calculated using multiple logistic regression in a group comprised of the 126 patients treated between January 2006 and March 2007 and the 24 patients treated with EPO; entering treatment with EPO as the dependent variable and age, male sex, witnessed arrest, time from call to start CPR, PEA, asystole, and bystander CPR as the pre-treatment covariates. For each EPO treated patient, two controls were selected by finding those with the propensity scores closest to the propensity score of the EPO treated patient within a ±0.015 range (D'Agostino R B, Jr. Propensity scores in cardiovascular research. *Circulation* 2007; 115:2340-2343). This group of 48 patients was designated as matched controls.

The same covariates used to calculate the propensity scores were used to adjust odds ratios for the comparison between EPO and the concurrent controls and between EPO and the matched controls.

Human Data Collection

Data were collected according to the Utstein style. For the initial rhythm, ventricular fibrillation or pulseless ventricular tachycardia was adjudicated when an automated external defibrillator (AED) discharged or when directly visualized by personnel carrying manual defibrillators. Pulseless electrical activity and asystole were adjudicated by personnel carrying manual defibrillators. $P_{ET}CO_2$ was recorded every minute during chest compressions to assess the hemodynamic efficacy of chest compression. A LIFEPAK® 12 defibrillator/monitor (Physio-Control, Inc., part of Medtronic, Inc.) was used for this purpose. Blood gases and chemistry along with troponin I, brain natriuretic peptide, hemoglobin, and hematocrit were measured in the ICU. The cerebral performance category was measured upon hospital discharge in patients who survived.

Results and Statistical Analysis of Human Study

SigmaStat for Windows version 3.0.1 was used. Odds ratios with 95% confidence intervals were calculated for the primary and secondary outcomes first unadjusted and then adjusted using multiple logistic regression. Differences between additional categorical variables were analyzed by Chi-square test or Fisher exact test. Differences between continuous variables were analyzed by unpaired t-test or by Mann-Whitney rank sum test if the test for normality or equal variance failed. The data are presented as mean with one standard deviation (SD) or median with interquartile range [IQR]. A two-tail P-value <0.05 was considered statistically significant. Because of the preliminary nature of the study, power and sample size calculations were not performed. The comparisons of EPO with each control group were considered independent analyses.

Figure 6:
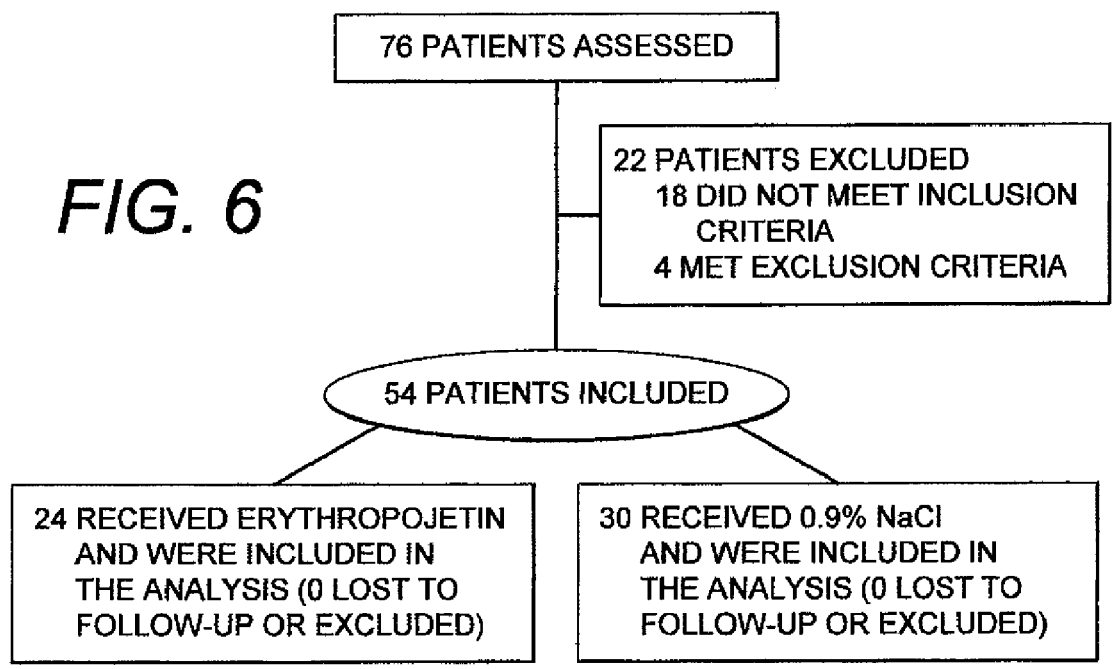
FIG. 6 is a schematic diagram showing the number of patients screened, included, and analyzed for the human study.

During the course of the prospective study (comparing EPO with concurrent controls) a total of 76 out-of-hospital cardiac arrests occurred. Twenty-two patients were excluded; 7 were older than 80 years of age; 9 had cardiac arrest precipitated by trauma, drowning, or hanging; 2 had terminal illness, and 4 had spontaneous circulation restored by electrical shocks and chest compression before administration of a vasopressor agent leaving 24 patients treated with EPO and 30 treated with 0.9% NaCl for the analysis (FIG. 6).

The pretreatment characteristics of the EPO group and the two comparison groups are shown in Table 1. The groups were adequately balanced with regards to age, sex, arrests in urban area, cardiovascular etiology, and percentage of CPR performed by the BLS team. However, concurrent controls had a lower percentage of witnessed arrests and had a less favorable distribution of the initial cardiac rhythm (i.e., lower percentage of ventricular fibrillation/ventricular tachycardia). In addition, concurrent controls had a longer median time from call to start CPR and a lower percentage of bystander CPR, but these differences were statistically insignificant. Matched controls were better balanced as expected given that most of the pretreatment variables were included in the propensity score. However, minor statistically insignificant differences were observed that favored the matched controls, such as lower median time from call to start CPR and higher percentage of ventricular fibrillation/ventricular tachycardia.

TABLE 1

Baseline and Pretreatment Characteristics.

| Characteristic | EPO (n = 24) | Concurrent controls (n = 30) | P Value | Matched controls (n = 48) | P Value |
|---|---|---|---|---|---|
| Age (y), mean (SD) | 59 (13) | 61 (14) | 0.532 | 60 (16) | 0.874 |
| Male sex, n (%) | 16 (67) | 20 (67) | 1.000 | 34 (71) | 0.717 |
| Cardiac arrest in urban area, n (%) | 20 (83) | 23 (77) | 0.736 | 42 (88) | 0.722 |
| Witnessed arrest, n (%)[1] | 23 (96) | 22 (73) | 0.033 | 46 (96) | 1.000 |
| Time from call to start CPR (mins), median [IQR] | 5.5 [4.0-7.0] | 6.5 [4.0-10.0] | 0.273 | 5.0 [4.0-7.0] | 0.900 |
| Cardiovascular etiology of arrest, n (%)[2] | 17 (71) | 24 (86) | 0.190 | 35 (73) | 0.852 |
| Initial cardiac rhythm, n (%) | | | 0.028 | | 0.480 |
| VF/VT | 12 (50) | 11 (37) | | 31 (65) | |
| PEA | 8 (33) | 4 (13) | | 12 (25) | |
| Asystole | 4 (17) | 15 (50) | | 5 (10) | |
| Bystander CPR, n (%) | 11 (46) | 7 (23) | 0.081 | 20 (42) | 0.736 |
| CPR by BLS team, n (%) | 10 (42) | 13 (43) | 0.902 | 19 (40) | 0.865 |

Abbreviations: EPO, erythropoietin; IQR, interquartile range; CPR, cardiopulmonary resuscitation; VF, ventricular fibrillation; VT, ventricular tachycardia; PEA, pulseless electrical activity; SD, standard deviation; BLS, basic life support; ROSC, return of spontaneous circulation.
[1]Witnessed by BLS team in one instance in each group.
[2]Two instances were undetermined in concurrent controls.

Figure 7:
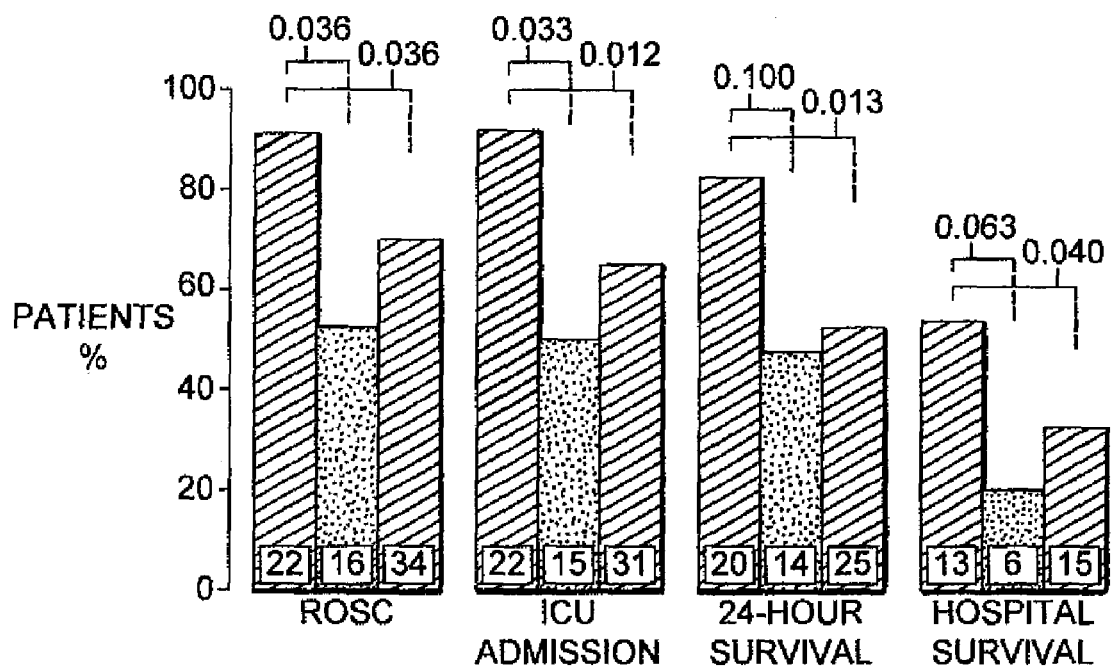
FIG. 7 is a graphical representation of resuscitation outcomes in human patients that received EPO (black bars, n=24) compared with concurrent controls (hatched bars, n=30) and with matched controls (gray bars, n=48). ROSC, return of spontaneous circulation; ICU, intensive care unit. Numbers inside bars denote patients for each outcome with the bar representing the percentage of the initial cohort. P-values were calculated by Wald statistics after adjustment by age, male sex, witnessed arrest, time from call to start CPR, pulseless electrical activity, asystole, and bystander CPR using multiple logistic regression.

The resuscitation outcomes are shown in Table 2 and FIG. 7. Compared with concurrent controls, the EPO group had higher rates of ICU admission (92% vs 50%), return of spontaneous circulation (92% vs 53%), 24-hour survival (83% vs 47%), and survival to hospital discharge (54% vs 20%). However, after adjustment for pretreatment covariates only ICU admission and return of spontaneous circulation remained statistically significant. Compared with matched controls, the EPO group had higher rates of ICU admission (92% vs 65%) and 24-hour survival (83% vs 52%) and statistically insignificant higher rates of return of spontaneous circulation (92% vs 71%) and survival to hospital discharge (54% vs 31%). However, these four outcome differences became statistically significant after adjustment for the pretreatment covariates. The relationship between the individual presenting rhythms and ICU admission is shown in Table 3 with each numerical difference favoring EPO; attaining statistical significance for asystole in EPO vs concurrent controls.

TABLE 3

ICU Admission According to Initial Cardiac Rhythm.

| Characteristic | EPO (n = 24) | Concurrent controls (n = 30) | P Value | Matched controls (n = 48) | P Value |
|---|---|---|---|---|---|
| VF/VT, n/Total (%) | 11/12 (92) | 8/11 (73) | 0.317 | 18/31 (58) | 0.067 |
| PEA, n/Total (%) | 7/8 (88) | 2/4 (50) | 0.236 | 10/12 (83) | 1.000 |
| Asystole, n/Total (%) | 4/4 (100) | 5/15 (33) | 0.033 | 3/5 (60) | 0.444 |

Abbreviations: ICU, intensive care unit; EPO, erythropoietin; VF, ventricular fibrillation; VT, ventricular tachycardia; PEA, pulseless electrical activity.

TABLE 2

Resuscitation Outcomes.

| Outcome | EPO (n = 24) n (%) | Concurrent controls (n = 30) | | | Matched controls (n = 48) | | |
|---|---|---|---|---|---|---|---|
| | | n (%) | P-Value Unadjusted & adjusted[1,2] | Odds Ratio (95% CI) Unadjusted & adjusted[2] | n (%) | P-Value Unadjusted & adjusted[1,2] | Odds Ratio (95% CI) Unadjusted & adjusted[2] |
| Primary outcome | | | | | | | |
| ICU admission | 22 (92) | 15 (50) | 0.004 / 0.033 | 11.0 (2.2-55.3) / 7.3 (1.2-45.7) | 31 (65) | 0.024 / 0.012 | 6.0 (1.3-28.8) / 18.7 (1.9-182.8) |
| Secondary Outcomes | | | | | | | |
| ROSC | 22 (92) | 16 (53) | 0.006 / 0.036 | 9.6 (1.9-48.4) / 7.4 (1.1-47.5) | 34 (71) | 0.060 / 0.036 | 4.5 (0.9-21.9) / 8.6 (1.1-64.5) |
| 24-hour survival | 20 (83) | 14 (47) | 0.008 / 0.100 | 5.7 (1.6-20.8) / 3.4 (0.8-14.3) | 25 (52) | 0.014 / 0.013 | 4.6 (1.4-15.5) / 6.1 (1.5-25.1) |
| Hospital survival | 13 (54) | 6 (20) | 0.011 / 0.063 | 4.7 (1.4-15.7) / 5.0 (0.9-26.9) | 15 (31) | 0.063 / 0.040 | 2.6 (0.9-7.1) / 3.2 (1.1-10.0) |

Abbreviations: EPO, erythropoietin; CI, confidence intervals; ICU, intensive care unit; ROSC, return of spontaneous circulation.
[1]Analized using Wald statistics.
[2]Adjusted by covariates with known predictive value (i.e., age, male sex, witnessed arrest, time from call to start CPR, pulseless electrical activity, asystole, and bystander CPR).

Figure 8:
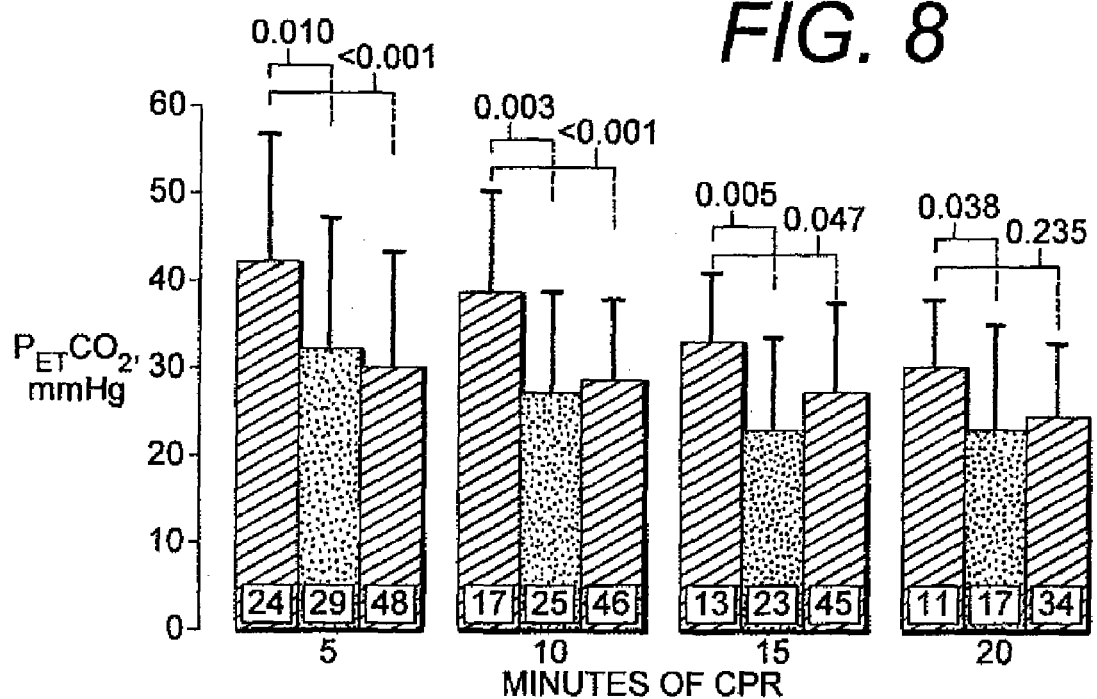
FIG. 8 is a graphical representation of end-tidal $PCO_2$ ($P_{ET}CO_2$) during cardiopulmonary resuscitation in patients who received EPO (black bars, n=24) compared with concurrent controls (hatched bars, n=30) and with matched controls (gray bars, n=48). Numbers inside bars denote patients remaining in cardiac arrest and receiving CPR. Data are presented as mean values with one standard deviation. P-values were calculated by unpaired t-test or by Mann-Whitney rank sum test for each time period and shown above bars.

Treatments during the resuscitation effort are shown in Table 4. Compared with concurrent controls, the EPO group received less 0.9% NaCl solution. Compared with matched controls, the EPO group received fewer doses of epinephrine and less 0.9% NaCl solution. In addition, compared with matched controls the median duration of the resuscitation effort was 12 minutes shorter in the EPO group when all patients were included and 13.5 minutes shorter when only those who had ROSC were included (Table 4). The $P_{ET}CO_2$ levels throughout chest compression are shown in FIG. 8, demonstrating higher levels in the EPO group compared with concurrent controls and matched controls.

TABLE 4

Drugs and Fluids Administered and Duration of the Resuscitation Effort.

| Characteristic | EPO (n = 24) | Concurrent controls (n = 30) | P Value | Matched controls (n = 48) | P Value |
|---|---|---|---|---|---|
| Drugs | | | | | |
| Vasopressin (IU), mean (SD), | 40 (0) | 41 (7) | 0.376 | | |
| median [IQR] | 40 [40-40] | | | 40 [40-40] | 0.890 |
| Epinephrine (mg), mean (SD), | 3.3 (2.8) | 4.4 (2.6) | 0.153 | | |
| median [IQR] | 3.0 [1.0-5.5] | | | 6.0 [3.0-7.0] | 0.003 |
| Atropine (mg), median [IQR] | 3 [0-3] | 3 [0-3] | 0.501 | 3 [0-3] | 0.671 |
| Theophylline (mg), median [IQR] | 0 [0-375] | 0 [0-250] | 0.972 | 0 [0-250] | 0.881 |
| Amiodarone (mg), median [IQR] | 0 [0-300] | 0 [0-0] | 0.298 | 300 [0-300] | 0.070 |
| Fluids | | | | | |
| 7.2% NaCl/6% HES (ml), median [IQR] | 250 [250-250] | 250 [250-250] | 0.923 | 250 [250-250] | 0.568 |
| 6% HES (ml), median [IQR] | 0 [0-250] | 0 [0-0] | 0.760 | 250 [0-500] | 0.068 |
| 0.9% NaCl (ml), median [IQR] | 0 [0-250] | 500 [0-500] | 0.042 | 500 [500-750] | <0.001 |
| Duration of CPR (mins), mean (SD), | 19.2 (12.8) | 23.9 (13.8) | 0.206 | | |
| median [IQR] | 17.0 [8.0-28.5] | | | 29.0 [18.0-33.5] | 0.006 |
| CPR to ROSC (mins), mean (SD), | 17.3 (115) | 16.0 (11.3) | 0.737 | | |
| median [IQR][1] | 13.0 [8.0-22.0] | | | 26.5 [16.0-32.0] | 0.010 |

Abbreviations: EPO, erythropoietin; IU, international units; SD, standard deviation; IQR, interquartile range; HES, hydroxyethyl starch.
[1]In patients who had return of spontaneous circulation.

Blood gases, chemistry, and biomarkers measured upon hospital admission are shown in Table 5. Compared with matched controls, the EPO group had higher arterial blood pH and $HCO_3^-$, and lower blood magnesium. No differences were noted in cerebral performance categories in survivors treated with EPO compared with either control group upon hospital discharge (Table 6).

TABLE 5

Blood Gases, Chemistry, and Biomarkers upon Hospital Admission.

| Characteristic | EPO (n = 24) | Concurrent controls (n = 30) | P Value | Matched controls (n = 48) | P Value |
|---|---|---|---|---|---|
| pHa (units), mean (SD), | 7.19 (0.18) | | | 7.02 (0.19) | 0.004 |
| median [IQR] | 7.21 [7.13-7.31] | 7.25 [7.13-7.29] | 0.839 | | |
| $PaCO_2$ (kPa), mean (SD), | 6.3 (2.2) | 5.9 (2.4) | 0.658 | | |
| median [IQR] | 5.5 [4.8-7.04] | | | 5.3 [4.5-6.1] | 0.084 |
| $PaO_2$ (kPa), median [IQR] | 13.7 [9.9-24.7] | 11.8 [9.8-20.2] | 0.956 | 11.7 [10.7-13.4] | 0.582 |
| $HCO_3^-$a (mmol/l), mean (SD), | 16.9 (5.5) | 16.1 (5.6) | 0.692 | | |
| median [IQR] | 17.9 [11.8-19.9] | | | 14.5 ] [12.4-15.3 | 0.035 |
| Lactate (mmol/l), median [IQR] | 4.6 [2.6-8.9] | 4.8 [3.9-7.3] | 0.754 | 5.9 ] [3.8-7.4 | 0.487 |
| Potassium (mmol/l), mean (SD), | 4.4 (0.7) | 4.8 (0.9) | 0.183 | | |
| median [IQR] | 4.5 [3.8-4.9] | | | 4.7 [3.9-5.1] | 0.365 |
| Sodium (mmol/l), mean (SD) | 142 (7) | 143 (5) | 0.825 | 140 (7) | 0.248 |
| Magnesium (mmol/l), median [IQR] | 0.8 [0.7-0.9] | 0.9 [0.7-0.9] | 0.729 | 0.9 [0.9-1.1] | <0.001 |
| Troponin I (µg/l), median [IQR] | 0.6 [0.2-12.6] | 1.0 [0.1-1.8] | 0.875 | 4.9 [2.2-15.0] | 0.052 |
| BNP (pmol/l), mean (SD), | 1039 (1226) | | | 1664 (715) | 0.085 |
| median [IQR] | 580 [23-2356] | 736 [350-2250] | 0.820 | | |

Abbreviations: EPO, erythropoietin; IQR, interquartile range; SD, standard deviation; BNP, brain natriuretic peptide.

TABLE 6

Cerebral Performance Categories (CPC)
in Survivors to Hospital Discharge.

| Category | EPO (n = 13) | Concurrent controls (n = 6) | Matched controls (n = 15) |
|---|---|---|---|
| | n (%) | | |
| CPC 1-2 | 9 (69) | 4 (67) | 11 (73) |
| CPC 3-4 | 4 (31) | 2 (33) | 4 (27) |

There were no statistically significant differences between categories. P-value 1.00 for each comparison.

Discussion of the Results of the Human Study

The study showed that administration of EPO in victims of out-of-hospital cardiac arrest during CPR improved the rates of return of spontaneous circulation, ICU admission, 24-hour survival, and hospital survival. This effect was associated with higher levels of $P_{ET}CO_2$ during chest compression; supporting the hypothesis that EPO improves resuscitation outcomes by enhancing the hemodynamic efficacy of CPR.

The study was originally designed as prospective and randomized. However, inability to secure uninterrupted supply of EPO forced investigators to allocate patients based on drug availability, precluding randomization and blinding during the prehospital phase. Although the possibility of investigator bias cannot be fully excluded, the highly favorable outcomes with EPO would argue against this possibility. Instead, differences in pretreatment covariates such as higher percentage of witnessed arrests, shorter response time, and higher incidence of ventricular fibrillation/ventricular tachycardia in the EPO group (Table 1) raised the possibility that these covariates—not EPO—accounted for the favorable outcomes. Indeed, adjusting for these covariates and others also relevant to resuscitation despite their lack of statistical significance reduced the odds ratios and removed the statistical significance from 24-hour survival and hospital survival. However, statistical significance remained for return of spontaneous circulation and ICU admission indicating that the beneficial effects of EPO on these outcomes were independent of the measured pretreatment covariates.

To further substantiate the effects of EPO we compared the EPO group with a group of 48 patients who had similar pretreatment characteristics. This group—designated matched controls—was selected using propensity scores from 126 patients who had episodes of out-of-hospital cardiac arrest within the 15-month period that preceded the original study and who had been managed with the same resuscitation protocol. The matched controls had pretreatment characteristics much closer to the EPO group than the concurrent controls (Table 1). However, small differences—albeit statistically insignificant—remained that favored matched controls, including a shorter response times and a higher incidence of ventricular fibrillation/ventricular tachycardia (Table 1). Adjustment for these and other pretreatment covariates increased the odds ratios and rendered statistically significant differences favoring EPO for return of spontaneous circulation, ICU admission, 24 hours survival, and hospital survival.

Accordingly, despite the limitations of the study the data support a beneficial effect of EPO during resuscitation from out-of-hospital cardiac arrest. The effects of EPO appeared similar for ventricular fibrillation/ventricular tachycardia, pulseless electrical activity, and asystole; however, a larger sample size would be required to establish whether the effects of EPO are modulated by the presenting rhythm.

The $P_{ET}CO_2$ during chest compression was higher in the erythropoietin group than in either of the two control groups. Because a uniform ventilation protocol was used, the higher $P_{ET}CO_2$ in the EPO group was consistent with the generation of higher forward blood flows (Duggal C, Weil M H, Gazmuri R J, Tang W, Sun S, O'Connell F, Ali M. Regional blood flow during closed-chest cardiac resuscitation in rats. *J Appl Physiol* 1993; 74:147-152; Gazmuri R J, von Planta M, Weil M H, Rackow E C. Arterial PCO2 as an indicator of systemic perfusion during cardiopulmonary resuscitation. *Crit. Care Med* 1989; 17:237-240; Orliaguet G A, Carli P A, Rozenberg A, Janniere D, Sauval P, Delpech P. End-tidal carbon dioxide during out-of-hospital cardiac arrest resuscitation: comparison of active compression-decompression and standard CPR. *Ann Emerg Med* 1995; 25:48-51; Kolar M, Krizmaric M, Klemen2 P, Grmec S. Partial pressure of end-tidal carbon dioxide successful predicts cardiopulmonary resuscitation in the field: a prospective observational study. *Crit. Care* 2008; 12:R115). This observation is in agreement with the hypothesis developed based on the rat experiments, proposing that EPO can prevent decreases in left ventricular myocardial distensibility during chest compression enabling hemodynamically more effective chest compression by preserving left ventricular preload (Singh D, Kolarova J D, Wang S, Ayoub I M, Gazmuri R J. Myocardial protection by erythropoietin during resuscitation from ventricular fibrillation. *Am J Ther* 2007; 14:361-368). Decreases in left ventricular myocardial distensibility have been described in humans as myocardial firmness (Takino M, Okada Y. Firm myocardium in cardiopulmonary resuscitation. *Resuscitation* 1996; 33:101-106). In these studies, the authors reported on 59 adult patients who suffered non-traumatic out-of-hospital cardiac arrest and underwent open-chest direct manual cardiac compression in the emergency department after failure of closed-chest resuscitation. A "firm" myocardium was noticed during manual cardiac compression in 36 cases affecting predominantly the left ventricle. In the remaining 23 cases the hearts were "soft." They also noted that some hearts became "firm" during compression. The presence of a "firm" myocardium was associated with reduced hemodynamic efficacy of cardiac compression as evidenced by a lower $P_{ET}CO_2$. Hearts with "very firm" myocardium never regained spontaneous contractions. Hearts with "less firm" myocardium showed some, albeit insufficient, spontaneous contractions. Hearts with "soft" myocardium regained contractions and were able to generate a peripheral pulse in most instances.

In various animal models, targeting ischemia and reperfusion injury by limiting sarcolemmal $Na^+$ entry prevents reductions in myocardial compliance also enabling hemodynamically more effective chest compression (Kolarova J D, Ayoub I M, Gazmuri R J. Cariporide enables hemodynamically more effective chest compression by leftward shift of its flow-depth relationship. *Am J Physiol Heart Circ Physiol* 2005; 288:H2904-H2911; Ayoub I M, Kolarova J D, Yi Z, Trevedi A, Deshmukh H, Lubell D L, Franz M R, Maldonado F A, Gazmuri R J. Sodium-hydrogen exchange inhibition during ventricular fibrillation: Beneficial effects on ischemic contracture, action potential duration, reperfusion arrhythmias, myocardial function, and resuscitability. *Circulation* 2003; 107:1804-1809; Kolarova J, Yi Z, Ayoub I M, Gazmuri R J. Cariporide potentiates the effects of epinephrine and vasopressin by nonvascular mechanisms during closed-chest resuscitation. *Chest* 2005; 127:1327-1334). Such effect was linked in recent studies to preservation of mitochondrial function (Ayoub I M, Kolarova J, Kantola R, Radhakrishnan J, Gazmuri R J. Zoniporide preserves left ventricular compliance during ventricular fibrillation and minimizes post-resuscitation myocardial dysfunction through benefits on energy metabolism. *Crit. Care Med* 2007; 35:2329-2336). EPO through non-genomic mechanisms can also protect mitochondrial function (Rafiee P, Shi Y, Su J, Pritchard K A, Jr., Tweddell J S, Baker J E. Erythropoietin protects the infant heart against ischemia-reperfusion injury by triggering multiple signaling pathways. *Basic Res Cardiol* 2005; 100:187-

197; Shi Y, Rafiee P, Su J, Pritchard K A, Jr., Tweddell J S, Baker J E. Acute cardioprotective effects of erythropoietin in infant rabbits are mediated by activation of protein kinases and potassium channels. *Basic Res Cardiol* 2004; 99:173-182; Nishihara M, Miura T, Miki T, Tanno M, Yano T, Naitoh K, Ohori K, Hotta H, Terashima Y, Shimamoto K. Modulation of the mitochondrial permeability transition pore complex in GSK-3beta-mediated myocardial protection. *J Mol Cell Cardiol* 2007; 43:564-570).

The favorable hemodynamic effects of EPO facilitated the resuscitation effort. When compared with matched controls, the EPO group was resuscitated 13.5 minutes earlier receiving fewer doses of epinephrine and less 0.9% NaCl solution, and manifested milder metabolic acidosis upon hospital admission. When compared with concurrent controls, the EPO group required less 0.9% NaCl and displayed a trend towards shorted CPR duration and fewer doses of epinephrine.

Accordingly, the various findings of this study show consistency among them. The improved resuscitation and survival outcomes associated with EPO were preceded by hemodynamically more effective chest compression—evidenced by a higher $P_{ET}CO_2$—which, in turn, facilitated return of spontaneous circulation in shorter time and with fewer resuscitation interventions.

Moreover, analyzing only those patients who had return of spontaneous circulation the percentage who survived in both control groups combined was 42% (21/50) whereas the percentage of those who survived in the EPO group was to 59% (13/22 unadjusted p=0.181). Accordingly, successful resuscitated using EPO could have an additional survival benefit. Such effect could be explained by an indirect benefit related to the faster return of spontaneous circulation with EPO and/or to a more direct effect of EPO related to additional tissue benefits leading to improved post-resuscitation myocardial and cerebral function.

Other Studies Assessing the Effects of Erythropoietin on Resuscitation

A total of five additional studies—four in rats (Huang C H, Hsu C Y, Chen H W, Tsai M S, Cheng H J, Chang C H, Lee Y T, and Chen W J. Erythropoietin improves postresuscitation myocardial dysfunction and survival in the asphyxia-induced cardiac arrest model. *Shock* 2007; 28:53-8; Popp E, Vogel P, Teschendorf P, and Bottiger B W. Effects of the application of erythropoietin on cerebral recovery after cardiac arrest in rats. *Am J Ther* 2007; 14:361-8; Huang C H, Hsu C Y, Tsai M S, Wang T D, Chang W T, and Chen W J. Cardioprotective effects of erythropoietin on postresuscitation myocardial dysfunction in appropriate therapeutic windows. *Crit. Care Med* 2008; 36:S467-S473; Incagnoli P, Ramond A, Joyeux-Faure M, Pepin J L, Levy P, and Ribuot C. Erythropoietin improved initial resuscitation and increased survival after cardiac arrest in rats. *Resuscitation* 2009; 80:696-700) and one in humans (Cariou A, Claessens Y E, Pene F, Marx J S, Spaulding C, Hababou C, Casadevall N, Mira J P, Carli P, and Hermine O. Early high-dose erythropoietin therapy and hypothermia after out-of-hospital cardiac arrest: a matched control study. *Resuscitation* 2008; 76:397-404)—have been reported examining the effects of EPO on resuscitation. In three of the animal studies, administration of EPO before induction of cardiac arrest (Incagnoli P, Ramond A, Joyeux-Faure M, Pepin J L, Levy P, and Ribuot C. Erythropoietin improved initial resuscitation and increased survival after cardiac arrest in rats. *Resuscitation* 2009; 80:696-700) or after restoration of spontaneous circulation (Huang C H, Hsu C Y, Chen H W, Tsai M S, Cheng H J, Chang C H, Lee Y T, and Chen W J. Erythropoietin improves postresuscitation myocardial dysfunction and survival in the asphyxia-induced cardiac arrest model. *Shock* 2007; 28:53-8; Huang C H, Hsu C Y, Tsai M S, Wang T D, Chang W T, and Chen W J. Cardioprotective effects of erythropoietin on postresuscitation myocardial dysfunction in appropriate therapeutic windows. *Crit. Care Med* 2008; 36:S467-S473) exerted beneficial myocardial effects leading to less post-resuscitation myocardial dysfunction with improved survival. In the other animal study (Popp E, Vogel P, Teschendorf P, and Bottiger B W. Effects of the application of erythropoietin on cerebral recovery after cardiac arrest in rats. *Resuscitation* 2007; 74:344-51) and in the human study (Cariou A, Claessens Y E, Pene F, Marx J S, Spaulding C, Hababou C, Casadevall N, Mira J P, Carli P, and Hermine O. Early high-dose erythropoietin therapy and hypothermia after out-of-hospital cardiac arrest: a matched control study. *Resuscitation* 2008; 76:397-404) the focus was on neurological outcome. In the animal study, EPO was given before cardiac arrest. In the human study, EPO was given after return of spontaneous circulation. However, neither study showed effects on neurological recovery. Similarly, the neurological outcome in our clinical study was not affected by EPO (Grmec S, Strnad M, Kupnik D, Sinkovic A, and Gazmuri R J. Erythropoietin facilitates the return of spontaneous circulation and survival in victims of out-of-hospital cardiac arrest. *Resuscitation* 2009; 80:631-7).

With regards to the single additional clinical study, it was conducted in France by Cariou and colleagues. This study enrolled a small group of patients who had suffered out-of-hospital cardiac arrest to examine possible neuroprotective effects of EPO. Five doses of 40,000 IU of EPO-alpha each were given over an interval of 48 hours to 18 patients who remained comatose with a Glasgow Come Scale of <7 after return of spontaneous circulation. The first dose of EPO was given at a median time of 62 minutes (42-75, IQR) after return of spontaneous circulation. The effects of EPO were compared with 40 contemporaneous matched controls. There were differences favoring EPO at 28 days in survival (55.0% vs 47.5%) and full neurological recovery (55.0% vs 37.5%), but the differences were statistically insignificant. The EPO group experienced a higher incidence of thrombocytosis (15% vs 5%) and one of these patients suffered an occlusion of a coronary stent.

Accordingly, whereas in this study the investigators examined the whether EPO given after return of spontaneous circulation could have neuroprotective effects, our work claims that EPO given during chest compression leads to higher rate of return of spontaneous circulation and survival with intact neurological function by mechanisms linked to preservation of left ventricular myocardial distensibility.

Erythropoietin Dose in Humans

The dose of EPO was empirically selected based on doses previously used in preclinical and clinical studies to activate cell protective mechanisms. In animals a dose of 5,000 IU/kg had been used effectively by us and other investigators (Bullard A J, Govewalla P, Yellon D M. Erythropoietin protects the myocardium against reperfusion injury in vitro and in vivo. *Basic Res Cardiol* 2005; 100:397-403; Nishihara M, Miura T, Miki T, Sakamoto J, Tanno M, Kobayashi H, Ikeda Y, Ohori K, Takahashi A, Shimamoto K. Erythropoietin affords additional cardioprotection to preconditioned hearts by enhanced phosphorylation of glycogen synthase kinase-3 beta. *Am J Physiol Heart Circ Physiol* 2006; 291:H748-H755; Singh D, Kolarova J D, Wang S, Ayoub I M, Gazmuri R J. Myocardial protection by erythropoietin during resuscitation from ventricular fibrillation. *Am J Ther* 2007; 14:361-368). The 90,000 IU used in the present study corresponded to approximately one-fourth the dose used in animals and one-and-a-half times the dose used in an ongoing clinical trial assessing the effects on acute myocardial infarction (Belonje A M, Voors A A, van Gilst W H, Anker S D, Slart R H, Tio R A, Zijlstra F, van Veldhuisen D J. Effects of erythropoietin after an acute myocardial infarction: rationale and study design of a prospective, randomized, clinical trial (HEBE III). *Am Heart J* 2008;

155:817-822). However, there is a paucity of information on the optimal dose of EPO and further dose-finding work would be warranted. Given that a single dose of EPO was administered, substantial effects on erythropoiesis were not anticipated. The hematocrit in the present study was not statistically different among groups at 48 hours and at 72 hours.

What is meant by "facilitating the resuscitation" in the present disclosure is an improvement of the resuscitation outcome by promoting hemodynamically more effective resuscitation such as, but is not limited to, preservation of left ventricular myocardial distensibility that can be evidenced by demonstrating increases in the ratio between the coronary perfusion pressure and the depth of compression and/or by ensuring better hemodynamic function post-resuscitation in which there is higher mean aortic pressure and cardiac work index. "Facilitating the resuscitation" can also be measured by other methods such as, but are not limited to, an improvement on the rate on initial resuscitation, and an improvement on the rate of survival of the subject.

What is meant by "concurrent" is that the EPO is administered at any time during the resuscitation, including any time between just immediately before cardiac resuscitation to the completion of the resuscitation procedure. In an embodiment, the EPO is administered just immediately before cardiac resuscitation. In another embodiment, the EPO is administered at the beginning of the resuscitation. In yet another embodiment, the EPO is administered during the cardiac resuscitation, which is any time between after the beginning of the resuscitation and before the end of the resuscitation procedure.

Though EPO was used in the present studies, other forms of EPO can be used in the place of EPO, which include but are not limited to any variants, fragments, conjugates, derivatives, and mutants of the EPO protein, produced by natural, recombinant, or synthetic means. The forms of EPO (which is used interchangeably in the present invention with EPO) that can be used in the present invention include but are not limited to: naturally-occurring, synthetic and recombinant forms of EPO from human or other mammalian species, as well as other EPO-related molecules. The term erythropoietin or EPO, therefore, includes any molecule which possesses EPO activities similar to those found in the naturally-occurring human EPO or any molecule that stimulates EPO activities, which includes but is not limited to: erythropoietin, asialo-erythropoietin, deglycosylated erythropoietin, erythropoietin analogs, erythropoietin mimetics, erythropoietin fragments, hybrid erythropoietin molecules, erythropoietin receptor-binding molecules, erythropoietin agonists, renal erythropoietin, brain erythropoietin, oligomers and multimers thereof, muteins thereof, and congeners thereof. The examples of the various forms of erythropoietin or EPO listed above also embrace the variants in the extents of and sites of glycosylation.

From the studies disclosed in the present application, it is evident that concurrent administration of an effective amount of EPO is effective in facilitating the resuscitation of a mammalian subject suffering from cardiac arrest when the EPO is administered concurrent with resuscitation and after the onset of the cardiac arrest. In a preferred embodiment, the mammalian subject is human. In another preferred embodiment, the cardiac arrest is due to ventricular fibrillation, pulseless electrical activity, or asystole.

What is meant by "an effective amount" of EPO is a dose of EPO from about 200 to about 6,000 IU/kg in mammalian rats. In a preferred embodiment, the effective amount in mammalian rats is about 5,000 IU/kg. An effective amount of EPO in the human patients is a bolus dose of about 1,200 IU/kg (i.e., 3 vials of 30,000 IU each prepared as one injection for an average size adult).

In the examples above, the EPO was administered in bolus dose into the right atrium through a centrally placed catheter in the case of the rat studies and intravenously through a peripheral vein in the case of the human subjects. Administration of EPO intravenously was followed by a 0.9% NaCl solution flush to secure mobilization of the EPO dose to a central cardiovascular location. However, EPO can also be administered by other routes, such as, but not limited to intraarterial (IA), intraperitoneal (IP), intracardiac (IC), and intraosseous (TO). In a preferred embodiment, EPO is administered intravenously or intraosseously. The administration can be in bolus or can be continuous. Formulation of the EPO will vary according to the route of administration selected. An appropriate formulation comprising EPO to be administered can be prepared in a physiologically acceptable vehicle or carrier and optional additional ingredients. "Acceptable vehicle or carrier" includes but is not limited to any and all solvents, dispersion media, antibacterial and antifungal agents, isotonic agents, and the like which are compatible with the activity of the EPO and are physiologically acceptable to the subject. "Additional ingredients" include, but are not limited to, one or more of the acceptable pharmaceutical excipients, which are well known to those skilled in the art in formulation.

As shown in our studies, in one embodiment one single dose of EPO is enough to accomplish the facilitation of cardiac resuscitation in the present disclosure.

"Resuscitation" in the present invention, also referred to as "cardiac resuscitation", includes one or more procedures to restore the pumping function of the heart, which may include but are not limited to manual, mechanical, or electrical procedures, or by chemical means (e.g., administration of epinephrine). A common manual procedure is cardiac compression by rhythmically pressing on the chess of the subject. Resuscitation can also be performed mechanically by devices designed to compress the chest directly like it is done manually or circumferentially utilizing a load-distributing band. Cardiac resuscitation is often accompanied by efforts to maintain oxygenation by artificially maintaining the breathing function of the lungs. This combined procedure is known as "cardiopulmonary resuscitation" or CPR in brief. An example of an electrical procedure is the use of a defibrillator in which electrical shocks are applied for the purpose of ending ventricular fibrillation. Resuscitation can be performed with the chest closed or with the chest open.

As mentioned earlier, the administration of EPO is concurrent with the resuscitation efforts. What is meant by "concurrent" is that the EPO is administered immediately before, at the beginning of, or during the resuscitation efforts but after the onset of cardiac arrest. Our data indicate that administration of EPO before onset of cardiac arrest is less effective.

While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from the novel aspects of the invention as defined in the claims. The appended claims should be construed broadly and in a manner consistent with the spirit and the scope of the invention herein.

We claim:

1. A method for facilitating cardiac resuscitation in a mammalian subject suffering from cardiac arrest comprising administration of an effective amount of erythropoietin (EPO), wherein the EPO is wildtype or recombinant EPO, to the subject concurrent with cardiac resuscitation and after the onset of cardiac arrest, wherein the administration of EPO to the mammalian subject increases the rate of return of spontaneous circulation compared to a mammalian subject resuscitated without EPO and wherein the administration of EPO shortens the duration of resuscitation to restore spontaneous circulation earlier when compared to mammalian subjects resuscitated without EPO.

2. The method of claim 1, wherein the mammalian subject is human.

3. The method of claim 1, wherein the EPO is a recombinant human EPO (rhEPO).

4. The method of claim 1, wherein the effective amount of EPO is from about 200 U/kg to about 6,000 U/kg.

5. The method of claim 1, wherein the effective amount of EPO is about 1,200 IU/kg.

6. The method of claim 1, wherein the cardiac resuscitation is manual, mechanical, electrical, chemical, or a combination thereof.

7. The method of claim 1, wherein the cardiac resuscitation is with a closed-chest or with an open-chest.

8. The method of claim 1, wherein the EPO is administered by a route selected from the group consisting of: intravenous (IV), intraarterial (IA), intraperitoneal (IP), intracardiac (IC), and intraosseous (IO).

9. The method of claim 1, wherein the administration of EPO is in bolus or continuous.

10. The method of claim 1, wherein the EPO is administered just immediately before cardiac resuscitation.

11. The method of claim 1, wherein, the EPO is administered at the beginning of cardiac resuscitation.

12. The method of claim 1, wherein the EPO is administered during cardiac resuscitation.

13. The method of claim 1, wherein the cardiac arrest is due to ventricular fibrillation, pulseless electrical activity, or asystole.

14. The method of claim 1, wherein administration of EPO to the mammalian subject results in increased survival compared to a mammalian subject resuscitated without EPO.

15. A method for improving the hemodynamic efficacy of chest compression during cardiopulmonary resuscitation by preserving left ventricular myocardial distensibility in a mammalian subject suffering from cardiac arrest comprising administration of an effective amount of erythropoietin (EPO), wherein the EPO is wildtype or recombinant EPO to the subject concurrent with cardiac resuscitation resulting in an increased amount of blood flow generated during each chest compression manifesting in an increased ratio of coronary perfusion pressure to depth of chest compression compared to a mammalian subject resuscitated without EPO.

* * * * *